United States Patent
Lee et al.

(10) Patent No.: US 8,864,831 B2
(45) Date of Patent: Oct. 21, 2014

(54) FIXATION OF ELASTOMER TO RIGID STRUCTURES

(75) Inventors: Casey K. Lee, Florham Park, NJ (US); George Makris, West Orange, NJ (US); Alastair J. T. Clemow, Princeton, NJ (US)

(73) Assignee: K2M, Inc., Leesburg, VA (US)

( * ) Notice: Subject to any disclaimer, the term of this patent is extended or adjusted under 35 U.S.C. 154(b) by 1548 days.

(21) Appl. No.: 11/814,369

(22) PCT Filed: Jan. 19, 2006

(86) PCT No.: PCT/US2006/001629
§ 371 (c)(1),
(2), (4) Date: Jul. 16, 2008

(87) PCT Pub. No.: WO2006/078662
PCT Pub. Date: Jul. 27, 2006

(65) Prior Publication Data
US 2008/0306609 A1    Dec. 11, 2008

Related U.S. Application Data

(60) Provisional application No. 60/693,430, filed on Jun. 24, 2005, provisional application No. 60/644,527, filed on Jan. 19, 2005.

(51) Int. Cl.
*A61F 2/44* (2006.01)
*A61B 17/72* (2006.01)
*A61F 2/30* (2006.01)
*A61F 2/08* (2006.01)

(52) U.S. Cl.
CPC ....... *A61B 17/72* (2013.01); *A61F 2202/30563* (2013.01); *A61F 2002/30574* (2013.01); *A61F 2220/0025* (2013.01); *A61F 2/3094* (2013.01); *A61F 2002/30971* (2013.01); *A61F 2/442* (2013.01); *A61F 2002/30014* (2013.01); *A61F 2002/087* (2013.01); *A61F 2002/305* (2013.01); *A61F 2002/30485* (2013.01); *A61F 2310/00023* (2013.01); *A61F 2/0811* (2013.01); *A61F 2002/30387* (2013.01); *A61F 2002/30616* (2013.01); *A61F 2002/30495* (2013.01); *A61F 2002/30069* (2013.01); *A61F 2250/0018* (2013.01); *A61F 2002/30604* (2013.01)
USPC .................................. 623/17.16; 623/17.11

(58) Field of Classification Search
USPC ..................... 623/17.11–17.16, 11.11, 23.58; 606/246–249
See application file for complete search history.

(56) References Cited

U.S. PATENT DOCUMENTS

| 3,867,728 A | 2/1975 | Stubstad et al. |
| 3,875,595 A | 4/1975 | Froning |

(Continued)

FOREIGN PATENT DOCUMENTS

| EP | 0 566 810 | 10/1993 |
| EP | 0 642 775 | 3/1995 |

(Continued)

OTHER PUBLICATIONS

Hellier WG et al., Spine 1992, 127(6 Suppl.): Ss86-96.

(Continued)

*Primary Examiner* — Pedro Philogene
*Assistant Examiner* — Christina Negrellirodrigue
(74) *Attorney, Agent, or Firm* — Miles & Stockbridge P.C.

(57) ABSTRACT

A surgical implant, especially an artificial intervertebral disc, includes a rigid substrate (513) having a porous attachment structure (512) that covers a portion of the substrate and an elastomeric body (510) that is fastened to the substrate by impregnating the porous attachment structure. The porous attachment structure has a net porosity greater than 21.5%. The porous attachment structure may be, for example, a perforated plate or a screen spaced from a substrate surface, or a layer of trabecular metal or an open-cellular material.

19 Claims, 9 Drawing Sheets

(56) References Cited

U.S. PATENT DOCUMENTS

| | | |
|---|---|---|
| 4,349,921 A | 9/1982 | Kuntz |
| 4,759,766 A | 7/1988 | Buettner-Janz et al. |
| 4,759,769 A | 7/1988 | Hedman et al. |
| 4,772,287 A | 9/1988 | Ray et al. |
| 4,863,477 A | 9/1989 | Monson |
| 4,904,260 A | 2/1990 | Ray et al. |
| 4,911,718 A | 3/1990 | Lee et al. |
| 4,932,969 A | 6/1990 | Frey et al. |
| 4,946,378 A | 8/1990 | Hirayama et al. |
| 5,047,055 A | 9/1991 | Bao et al. |
| 5,071,437 A | 12/1991 | Steffee |
| 5,123,926 A | 6/1992 | Pisharodi |
| 5,171,281 A | 12/1992 | Parsons et al. |
| 5,192,326 A | 3/1993 | Bao et al. |
| 5,258,031 A | 11/1993 | Salib et al. |
| 5,306,308 A | 4/1994 | Gross et al. |
| 5,306,309 A | 4/1994 | Wagner et al. |
| 5,314,477 A | 5/1994 | Marnay |
| 5,314,478 A | 5/1994 | Oka |
| 5,320,644 A | 6/1994 | Baumgartner |
| 5,370,697 A | 12/1994 | Baumgartner |
| 5,401,269 A | 3/1995 | Buttner-Janz et al. |
| 5,458,642 A | 10/1995 | Beer |
| 5,458,643 A * | 10/1995 | Oka et al. .................... 623/17.16 |
| 5,514,180 A | 5/1996 | Heggeness et al. |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,674,294 A | 10/1997 | Bainville et al. |
| 5,674,296 A | 10/1997 | Bryan et al. |
| 5,676,702 A | 10/1997 | Ratron |
| 5,683,465 A | 11/1997 | Shinne et al. |
| 5,824,093 A | 10/1998 | Ray et al. |
| 5,824,094 A | 10/1998 | Serhan et al. |
| 5,865,846 A | 2/1999 | Bryan et al. |
| 5,888,226 A | 3/1999 | Rogozinski |
| 5,893,889 A | 4/1999 | Harrington |
| 5,958,314 A * | 9/1999 | Draenert ................. 264/42 |
| 5,976,186 A | 11/1999 | Bao et al. |
| 6,110,210 A * | 8/2000 | Norton et al. ............. 623/17.16 |
| 6,113,637 A | 9/2000 | Gill et al. |
| 6,113,640 A * | 9/2000 | Tormala et al. ........... 623/18.11 |
| 6,136,031 A | 10/2000 | Middleton |
| 6,139,579 A | 10/2000 | Steffee |
| 6,156,067 A | 12/2000 | Bryan et al. |
| 6,162,252 A * | 12/2000 | Kuras et al. ............... 623/17.16 |
| 6,187,043 B1 | 2/2001 | Ledergerber |
| 6,187,048 B1 | 2/2001 | Milner et al. |
| 6,224,607 B1 | 5/2001 | Michelson |
| 6,296,664 B1 | 10/2001 | Middleton |
| 6,315,797 B1 | 11/2001 | Middleton |
| 6,348,071 B1 | 2/2002 | Steffee et al. |
| 6,368,350 B1 | 4/2002 | Erickson et al. |
| 6,395,032 B1 | 5/2002 | Gauchet |
| 6,419,704 B1 | 7/2002 | Ferree |
| 6,419,706 B1 | 7/2002 | Graf |
| 6,482,234 B1 | 11/2002 | Weber et al. |
| 6,527,804 B1 | 3/2003 | Gauchet et al. |
| 6,533,818 B1 | 3/2003 | Weber et al. |
| 6,548,569 B1 * | 4/2003 | Williams et al. ............. 523/124 |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,592,624 B1 | 7/2003 | Fraser et al. |
| 6,607,558 B2 | 8/2003 | Kuras |
| 6,626,943 B2 | 9/2003 | Eberlein et al. |
| 6,645,248 B2 | 11/2003 | Casutt |
| 6,656,224 B2 | 12/2003 | Middleton |
| 6,669,732 B2 | 12/2003 | Serhan et al. |
| 6,682,562 B2 | 1/2004 | Viart et al. |
| 6,726,720 B2 | 4/2004 | Ross et al. |
| 6,733,532 B1 | 5/2004 | Gauchet et al. |
| 6,740,093 B2 * | 5/2004 | Hochschuler et al. .......... 606/94 |
| 6,740,118 B2 | 5/2004 | Eisermann et al. |
| 6,749,635 B1 | 6/2004 | Bryan |
| 6,893,465 B2 | 5/2005 | Huang |
| 7,169,181 B2 | 1/2007 | Kuras |
| 7,250,060 B2 | 7/2007 | Trieu |
| 2001/0016773 A1 | 8/2001 | Serhan et al. |
| 2001/0032017 A1 | 10/2001 | Alfaro et al. |
| 2001/0051829 A1 | 12/2001 | Middleton |
| 2002/0022888 A1 | 2/2002 | Serhan et al. |
| 2002/0077701 A1 | 6/2002 | Kuslich |
| 2003/0045939 A1 | 3/2003 | Casutt |
| 2003/0074066 A1 | 4/2003 | Errico et al. |
| 2003/0100951 A1 | 5/2003 | Serhan et al. |
| 2003/0135277 A1 | 7/2003 | Bryan |
| 2003/0208271 A1 | 11/2003 | Kuras |
| 2004/0122517 A1 | 6/2004 | Kuras et al. |
| 2004/0122518 A1 | 6/2004 | Rhoda |
| 2004/0167626 A1 | 8/2004 | Geremakis |
| 2004/0193273 A1 | 9/2004 | Huang |
| 2004/0249462 A1 | 12/2004 | Huang |
| 2004/0267367 A1 | 12/2004 | O'Neil |
| 2005/0131544 A1 | 6/2005 | Kuras |
| 2006/0229724 A1 | 10/2006 | Lechmann |
| 2006/0265075 A1 | 11/2006 | Baumgartner |
| 2006/0276900 A1 | 12/2006 | Carpenter |

FOREIGN PATENT DOCUMENTS

| | | |
|---|---|---|
| FR | 2 784 291 A1 | 4/2000 |
| JP | 03-501810 A | 4/1991 |
| JP | 06-285099 A | 11/1994 |
| JP | 08-004606 B | 1/1996 |
| JP | 3007903 B2 | 2/2000 |
| WO | WO 89/03663 a1 | 5/1989 |
| WO | WO 90/11740 A1 | 10/1990 |
| WO | WO 95/19153 A1 | 7/1995 |
| WO | WO 99/22675 A1 | 5/1999 |
| WO | WO 03/090650 A1 | 11/2003 |
| WO | WO 2004/033516 | 4/2004 |
| WO | WO 2004/039291 A1 | 5/2004 |
| WO | WO 2005/072660 | 8/2005 |
| WO | WO 2005/007041 A1 | 12/2005 |

OTHER PUBLICATIONS

Fraser RD et al., Spine J. 2004, 4(6S): 245s-251s.
Szpalski M, Eur. Spine J. (2000), 11(Suppl.2): S65-84.
Mcafee, P. et al., Spine J. 4:48s, 2004.
Hawkins MV et al., J. Orthop. Res. 12: 119-127, 1994.
Closkey RF et al., Spine 18(8): 1011-1015, 1993.
Langrana NA et al.,Spine J. 4 (2004), 245S-251S.

* cited by examiner

FIXATION OF ELASTOMER TO RIGID STRUCTURES

CROSS-REFERENCE TO RELATED APPLICATIONS

This application claims the benefit of U.S. Provisional Application No. 60/693,430, filed Jun. 24, 2005, the entire disclosure of which is incorporated herein by reference, and the benefit of U.S. Provisional Application No. 60/644,527, filed Jan. 19, 2005, the entire disclosure of which is incorporated herein by reference.

BACKGROUND OF THE INVENTION

1. Field of the Invention

This invention relates to articles having an elastomer fixed to a substrate of a rigid material such as a metal, and more particularly to orthopedic devices having elastomeric members bonded to rigid members, such as prostheses for replacing a mammalian intervertebral spinal disc, implants for artificial joints, prosthetic ligaments and tendons, and the like, wherein an elastomeric member is firmly bonded to a rigid endplate or other structure for attachment to bone.

2. Background Art

Low back pain is a very common pathological condition, affecting approximately 80% of the general population at some time. Although most patients experience the painful symptoms only occasionally and recover fully, approximately 10% of these patients come to experience chronic and disabling low back pain in spite of various medical treatments.

The most common cause of chronic disabling low back pain is degeneration of one or more of the intervertebral discs that are positioned between the vertebrae of the spine and permit the various natural movements of the spinal column. Such degenerative disc disease (DDD) may become intractable to non-surgical treatment and have to be treated by surgical intervention. Spinal fusion has been a traditional and generally effective treatment method for chronic disabling low back pain that is not responding to non-operative treatments. More recently, alternative treatments involving replacement of the entire disc or its nucleus have been developed for treatment of discogenic pain.

The first generation of prostheses for replacement of degenerated intervertebral discs has generally incorporated mutually sliding surfaces of relatively hard materials to provide for the required intervertebral motion in flexion, extension, lateral bending and torsion. Although such prostheses have been found to be helpful, improvements in shock absorption and replication of the natural motion of the intact intervertebral disc have been sought.

Accordingly, subsequently developed prostheses have incorporated elastomeric members in order to provide for the required motion and shock absorption. Such prostheses typically include relatively hard endplates for contacting the endplates of adjacent vertebrae and fixing the prosthesis thereto, together with an elastomeric disc core, positioned between the hard endplates and attached thereto.

Attachment of the elastomeric core of such prostheses to their hard endplates has hitherto been accomplished generally by adhesives, by mechanical interlocking undercuts or the like, or by providing a porous surface on the hard endplate which engages the elastomeric core, or combinations of such techniques. For example, it has been proposed to cover the surface of the endplate that contacts the elastomeric core with a coating of small generally spherical beads bonded to that surface, e.g., by sintering or the like. The elastomeric core may then be molded against the bead-covered surface, or otherwise applied thereto, whereby the elastomer infiltrates the porous bead coating and provides a substantial mechanical interlock between the hard endplate and the elastomeric core. Such bonding surfaces are disclosed, e.g., in U.S. Pat. No. 5,071,437.

Nevertheless, a need has continued to exist for alternative methods of securing hard elements of orthopedic devices, such as an endplate of an intervertebral disc prosthesis, to elastomeric elements such as the elastomeric core of an intervertebral disc prosthesis.

SUMMARY OF THE INVENTION

According to one of its basic principles, the present invention provides devices and methods in which an elastomeric member is securely fastened to a substrate by impregnating an attachment structure defining an assembly of apertures surrounded by solid bridges, integral with the substrate and extending across at least a substantial portion of a surface of the substrate, with at least a portion of the bridges being sufficiently spaced from an underlying portion of the substrate to provide a layer of elastomer underlying the bridges that is strong enough to resist disruption by tensile forces directed generally normal to the surface.

In particular embodiments, the attachment structure may be provided by a perforated plate, a screen, trabecular metal, porous metal, posts or fins upstanding from the surface and provided with lateral apertures, or the like, and is preferably made of a generally rigid material. Although not strictly limited in principle, the invention is most preferably applied to surgical implants.

Thus, according to one of its principal aspects, the invention provides a surgical implant, comprising a rigid surgical implant substrate, a porous attachment structure provided on the substrate and covering a portion of substrate, and an elastomeric body having a portion adjacent to the portion of the substrate and impregnating the porous attachment structure, the portion of the elastomeric body filling a major portion of a volume adjacent to the portion of the substrate and containing the porous attachment structure, whereby the elastomeric body is secured to the substrate.

According to another of its principal aspects, the invention provides a surgical implant, comprising a rigid surgical implant substrate, a porous attachment structure provided on the substrate and covering a portion of the substrate, and an elastomeric body having a portion adjacent to the portion of the substrate and impregnating the porous attachment structure, wherein throughout a thickness of the porous attachment structure in planes generally parallel to the portion of the substrate, a net porosity of the porous structure is greater than 21.5%.

In yet another of its aspects, the invention provides a method of manufacturing a surgical implant, comprising providing a rigid substrate member of the surgical implant, providing a porous attachment structure, attaching the porous attachment structure to the rigid substrate member, and impregnating the porous attachment structure with an elastomer to secure the elastomer to the rigid substrate member.

The foregoing and other aspects of the invention will be more fully appreciated from the detailed description which follows.

DETAILED DESCRIPTION OF THE INVENTION AND PREFERRED EMBODIMENTS

The invention provides a method of attaching a member of flexible elastomeric material to a rigid structure in a medical implant so that the attachment of the elastomeric member is strong enough to withstand the loads of its intended application. In a number of preferred embodiments, the invention achieves this goal by providing an article incorporating a porous structure, which may be rigid, the porous structure comprising open pores bounded by solid material and being spaced from a surface of a rigid substrate member to provide sufficient space between the porous structure and the surface for the elastomeric material to form a continuous body or bridge of elastomeric material between at least some of the elastomer-filled pores, whereby the elastomeric material cannot be mechanically detached from the implant without rupturing the body of elastomeric material. Preferably, the porosity of the porous structure is greater than 21.5%, i.e., the projected area of the pores on the substrate surface underlying the porous structure constitutes more than 21.5% of the area of the underlying surface.

In one preferred embodiment, the porous structure is spaced from the surface to provide a continuous uninterrupted layer or sheet of elastomer between the porous structure and the surface. Again, it is preferred that the porous structure have an interconnecting porosity greater than 21.5% by area, with porosity more typically running in the range of 30% to 80%.

In one particular form, the elastomer is secured to a rigid metal support or plate by means of perforations in the support or plate which allow the elastomer, when molded onto the support, to penetrate through to the back side of the support and form a continuous body between at least some of the elastomer-filled perforations. The number and size of these perforations, and therefore their cross sectional area, can be varied to the match the respective strengths of the elastomer and the metal. For instance, if the strength of the metal is 10 times that of the elastomer and the perforations occupy 90% of the available cross sectional area, then the polymer within the perforations will have the same load bearing capacity as the remaining metal.

Preferred devices prepared utilizing the present invention achieve a strong fixation of an elastomeric member to a rigid substrate by incorporating:

1) a two-dimensional or three-dimensional lattice structure, preferably having greater than 21.5% interconnecting porosity, so that the amount of elastomer within the lattice is greater than can be achieved using conventional beaded coatings and the like; and 2) preferably, a continuous bridge or layer of elastomer on the surface of the lattice furthest from the main body of the elastomeric member, whereby such a bridge or layer provides a strong bond between the portions of the elastomer within the lattice. Such a bridge or layer of elastomer supports the elastomer portions within the lattice and helps them to resist deformation under load, which could allow them to be pulled out of the lattice, with consequent failure of the attachment between elastomer and substrate and accompanying failure of the medical device. Such a bridge or layer may be formed by providing structure in the lattice around which the elastomer may loop, with consequent formation of a continuous band of elastomer connecting adjacent pores. Alternatively, a supporting layer of elastomer may be formed by providing an uninterrupted layer of elastomer on the surface of the porous structure that faces the substrate surface so that the elastomer material completely penetrates the porosity. Such a continuous layer of polymer, continuous with the polymer in the pores of the porous structure, provides a bond that helps to prevent the elastomer from being pulled out of the lattice.

The rigid fixation may utilize a two-dimensional lattice structure such as a perforated plate, perforated fin, wire mesh, or looped wire, or a three dimensional lattice structure such as open cell foam, trabecular metal porous surface or other high porosity structure having at least a major portion that is embedded in the elastomer.

Such lattice structures are preferably constructed to exhibit a net captive porosity greater than 21.5% (calculated as the total projected area of elastomer traversing through the pores or openings formed by the preferably rigid fixation structure divided by the combined projected area of rigid structure and elastomer). From one point of view, the elastomer material impregnating the pores or openings of the rigid lattice structure connects back to the main elastomer body in a continuous loop or the like. From another point of view, the elastomer impregnating the pores connects the main elastomer body to a continuous elastomer layer covering the opposite side of the rigid lattice structure. Such a configuration of lattice and elastomer produces a secure and stable assembly of elastomer and rigid lattice structure.

Another preferred article of the invention is an intervertebral disc prosthesis incorporating an elastomeric disc core secured to rigid endplates, wherein the flexible elastomer is molded onto a rigid (metal, polymer, composite, or ceramic) perforated plate member, and where the elastomer extends from one side of the plate member, though the perforations and reconnects to itself. The size, shape and location of these perforations can be controlled to obtain a desired fixation strength. The net captive porosity may be calculated for certain geometries. For example, a square plate region of unit side length L with a single central circular hole of diameter 0.95 L therein will exhibit a net captive porosity of about 71%. Similarly, if such a region is provided with a square hole having sides equal to 0.95 L, the net captive porosity will be about 90%. In both such examples, the minimum cross section of the metal surrounding the hole will be the same, i.e., 0.025 L. On the contrary, for a layer of closely compacted beads having a diameter L, the net captive porosity would be less than 21.5%.

In a given embodiment, the number, location and size of the perforations in a perforated plate can be modified depending on the elastomer and the load conditions. The holes are preferably made to have smooth edges to avoid cutting action on the polymer connections during repetitive tensile and compressive loading. The thickness of a continuous layer of elastomer on the side of the perforated rigid plate opposite the main body of the elastomeric member can be modified according to the tensile strength of elastomeric material.

In an intervertebral disc prosthesis according to the invention using an elastomeric disc core, typical loading conditions result in the highest tensile stress developing at the outermost regions (the anterior and posterior regions) of the elastomeric core during flexion and extension. Additionally, the stiffness differential between the rigid and flexible materials introduces an additional stress concentration factor. In such a prosthesis, the stress tending to pull the rigid endplate from the elastomeric core in the highly stressed peripheral regions may be reduced by extending the elastomeric core peripherally beyond the edge of the rigid endplate and crimping the extended portion to the peripheral edge region of the rigid endplate. This compressive preload of the free extension of the elastomer counteracts the tensile loads and helps to shield the outermost portion of the elastomeric core from the tensile disassociative stresses. Such crimping would have little or no contribution to the flexural stiffness of the disc but would provide for a significantly stronger fixation at these highly stressed regions.

Figure 1:
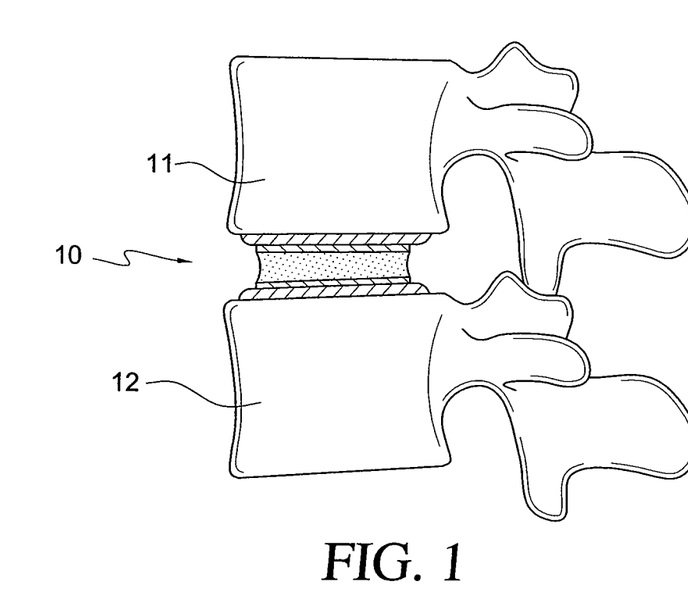
FIG. 1 is a schematic lateral view of an intervertebral disc prosthesis of the invention implanted between adjacent vertebral bodies.

The invention may be further illustrated by the structure of an artificial intervertebral disc prosthesis intended to replace a damaged or degenerated spinal disc in a human spinal column. FIG. 1 illustrates schematically an intervertebral disc prosthesis 10 implanted between adjacent upper and lower vertebrae 11 and 12 in a human spinal motion segment.

Figure 2:
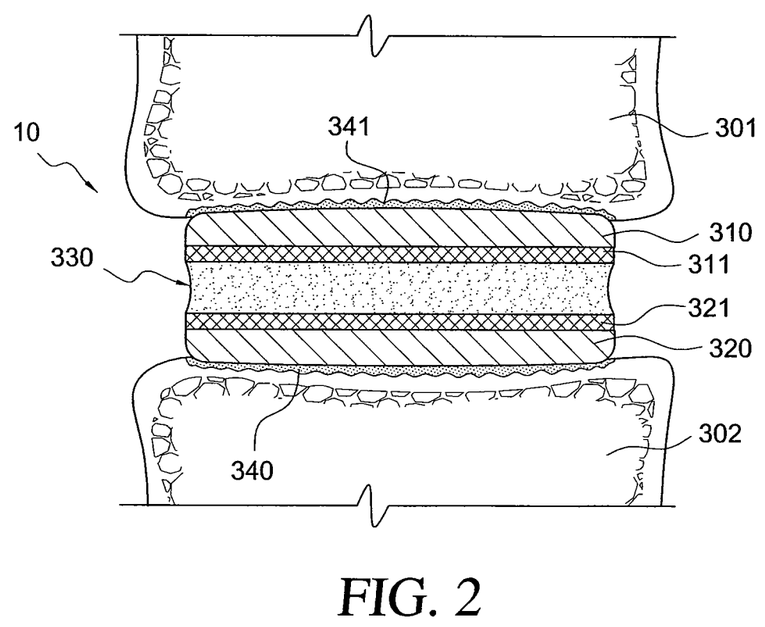
FIG. 2 is a sectional view of a preferred embodiment installed between adjacent vertebral bodies.

FIG. 2 is a more detailed cross-sectional view of the disc prosthesis 10, showing a first or upper rigid plate 310, a second or lower rigid plate 320, and a flexible elastomeric core 330 interposed between and fixedly assembled to the two rigid plates by rigid fixation means 311 and 321. For the disc prosthesis 10, the upper and lower rigid plates 310 and 320 are generally similar to each other, and the disc prosthesis 10 is symmetrically placed about a midline vertical plane. Rigid plates 310 and 320 are intended for fixation to the vertebral bones 301 and 302 by various generally conventional fixation means 340 and 341 (e.g., porous surface coating). Rigid plates 310 and 320 are made of biocompatible material, and preferably a metal such as Ti6Al4V (Ti-6% Al-4% V). Common metal fabrication methods may be used to fabricate rigid plates 310 and 320.

Figure 3A:
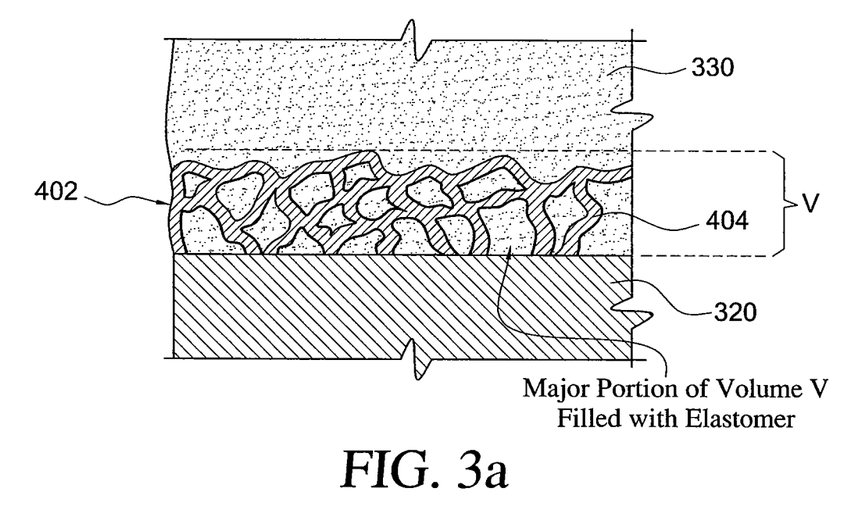
FIG. 3a is a partial detail sectional view illustrating the use of trabecular metal mechanical fixation means.

FIG. 3a is a detail view of a rigid fixation means suitable for use in the embodiment of FIG. 2, illustrating a preferred configuration of the fixation means wherein a trabecular metal porous structure 402 is used to produce porosity larger than 21.5% (projected area basis). The porous structure 402 is attached to endplate 320 by conventional means and provides for elastomer 330 to extend through high net captive porosity 404 from the flexible core region 330 to impregnate the porous structure 402 and interconnect with itself therein, thereby forming an integral connection back to core region 330, the porous structure 402 thus being embedded in the elastomer. Since the typical material strength of the elastomer is about one-fifth that of the rigid porous structure 402, the ratio of elastomer to metal could conveniently be about 80% (projected area basis) to provide a satisfactory bond between the core region 330 and the rigid substrate plate 320.

Figure 3B:
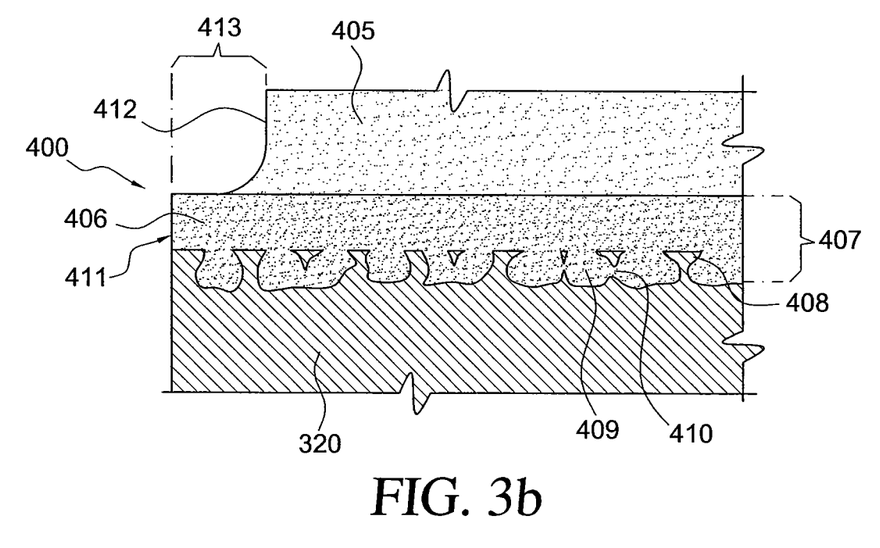
FIG. 3b is a partial detail sectional view illustrating the use of open cell foam metal mechanical fixation means.

FIG. 3b illustrates an alternate embodiment of the prosthesis of FIG. 3a, wherein the elastomeric core 400 is comprised of soft elastomeric material 405 and a harder elastomeric material 406 forming a transition plate 407. Transition plate 407 is fixed to the rigid substrate plate 320 by impregnation of a porous structure 408, e.g., an open cell porous structure as illustrated, to provide mechanical fixation. Such porous cell structures may be formed by conventional procedures, e.g., such as used to form patterned substrate surfaces by chemical or electrochemical etching, optionally using patterned photoresist layers, and the like. The elastomeric material 406 occupies the spaces within the porous structure 408 and, because of the porosity 410, forms a mechanical connection. This embodiment is additionally provided with a flange 411 that extends laterally beyond the vertical wall 412 of the elastomeric core 405. Similarly, porous structure 408 may be extended laterally a distance 413 for additional mechanical fixation. Because an intervertebral prosthesis experiences maximum stresses at the outer rim of the vertical wall 412 during bending of the vertebral column, flange 411 may be provided to further disperse these loads over a wider area, and minimizes stress concentration developed due to the different stiffness between elastomer 406 and rigid porous structure 408. Such a flange and porous structure extension may be used with all embodiments of the invention disclosed herein and will not be separately discussed in connection with other embodiments.

Figure 4A:
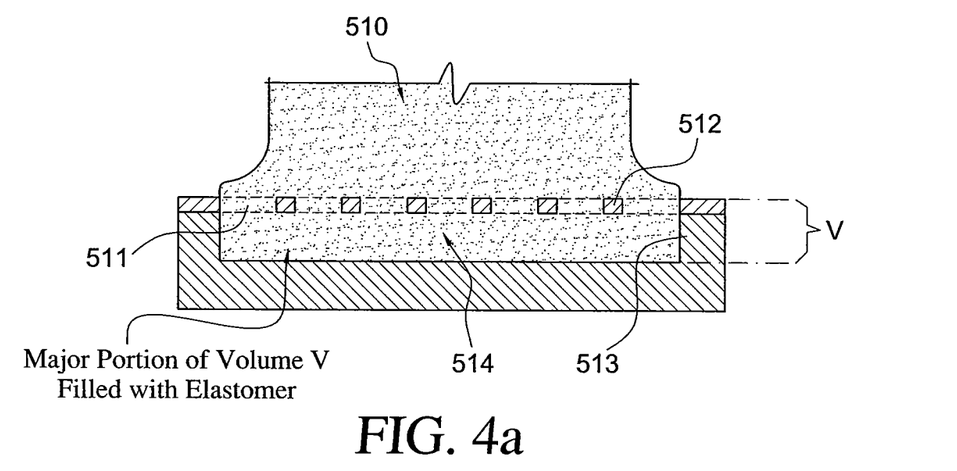
FIG. 4a is a partial detail sectional view illustrating the use of perforated plate mechanical fixation means.
Figure 4B:
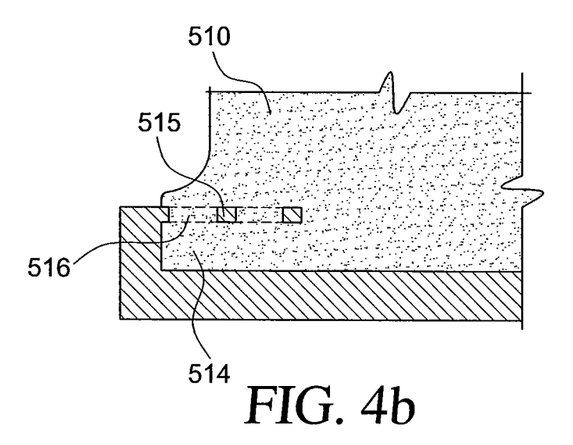
FIG. 4b is a partial detail sectional view illustrating the use of perforated peripheral flange mechanical fixation means.

The embodiments described above illustrate the use of highly porous structures affixed to the substrate. Such structures can present challenges due to manufacturing difficulties and high costs associated with quality control and processing. Accordingly, FIG. 4a illustrates an alternate embodiment wherein secure and stable fixation is achieved by the use of elastomer 510 extending though perforations 511 in a rigid structure (e.g., a plate) 512 attached to rigid substrate (e.g., metal endplate of an intervertebral prosthesis) 513. Elastomer material extends through perforated holes 511 from the main elastomer core 510 and forms a substantially continuous elastomeric layer or sheet 514 on the opposite side of rigid structure 512. Rigid structure 512 and perforations 511 may be in the form of a perforated plate as illustrated in FIG. 4a, or other similarly constructed structures having other opening geometries and orientations. FIG. 4b illustrates in detailed section an additional alternate embodiment having a horizontal peripheral flange 515 constituting the rigid fixation means and having a series of perforations 516. Elastomer 510 extends though perforations 516 and is connected back to the main polymer core on the opposite side of the flange as indicated generally at 514.

Figure 4C:
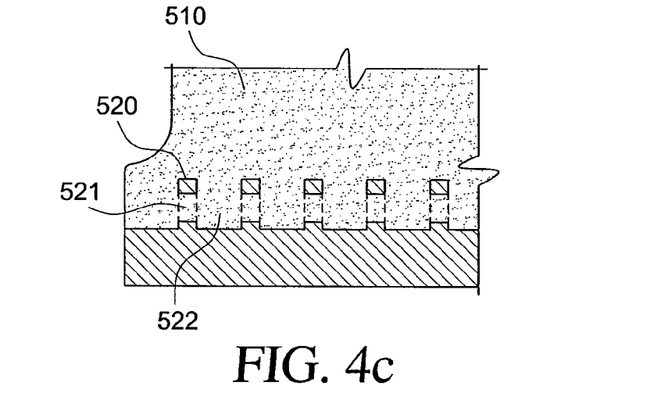
FIG. 4c is a partial detail sectional view illustrating the use of perforated rib mechanical fixation means extending vertically into the elastomeric core.

FIG. 4c illustrates another embodiment having one or more flanges or ribs 520 extending generally vertically from the surface of a substrate, protruding into the flexible elastomeric core 510, and having perforations 521 extending generally laterally through flanges 520. In a manner similar to that of the embodiment illustrated in FIG. 4b, elastomer material extends through the perforations 521, whereby the elastomer material forms a substantially continuous body with the elastomer material 522 along the sides of the flange 520.

Figure 4D:
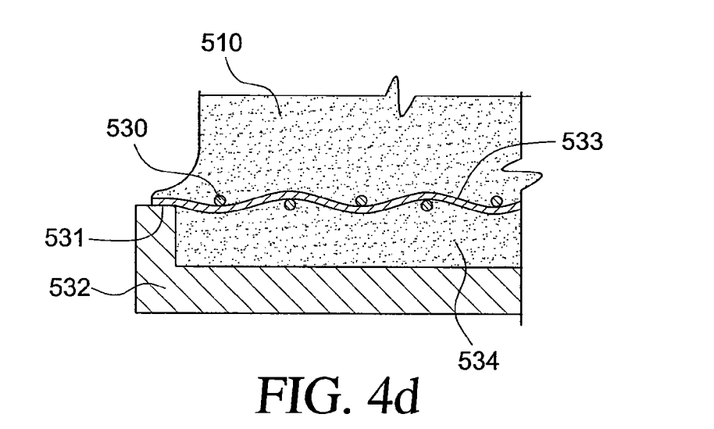
FIG. 4d is a partial detail sectional view illustrating the use of wire mesh mechanical fixation means.
Figure 4E:
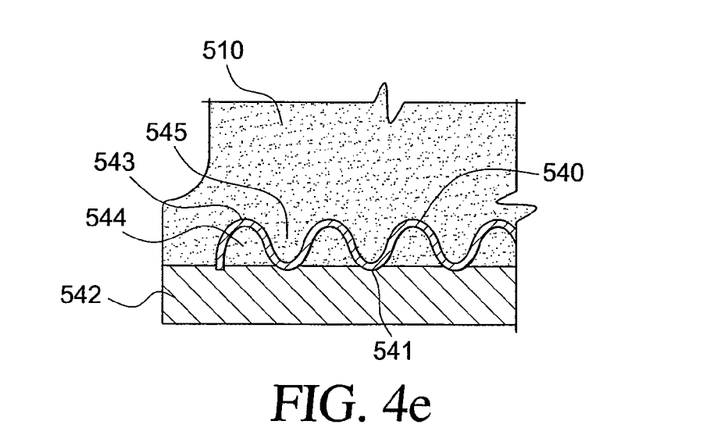
FIG. 4e is a partial detail sectional view illustrating the use of looped wire mechanical fixation means.

FIG. 4d illustrates an alternate embodiment wherein a wire mesh 530 is affixed to the rigid substrate 532, and spaced from the surface thereof by attachment to a generally vertical peripheral rim at 531. Elastomer 510 extends from the first side 533 of wire mesh 530 though the captive porosity of the mesh and forms a continuous layer or sheet 534 of elastomer on the opposing side of wire mesh 530. Alternatively, a wire structure may be formed as illustrated in FIG. 4e by attachments 541 of a structure containing upstanding wire loops 540 to the surface of the substrate 542. In this embodiment elastomer 510 extends from a region 545 and first side 543 of wire loops 540 though the captive porosity, as indicated at 544, and back to itself, thereby forming a continuous body of elastomer through the wire loops 540. The embodiment of FIG. 4e may also be provided with additional fixation strength by employing an elastomeric core with a harder transition plate and/or with a laterally extending flange as shown in the embodiment of FIG. 3b.

An elastomeric member, e.g., an elastomeric core of an intervertebral prosthesis, may be fixed to a rigid substrate, e.g., a metal endplate of such a prosthesis, by means of interfitting or mating structures, thereby forming a modular structural assembly. Conventional methods for assembling such modular structures include press fits, grooves, and interference locking or dovetail fixation mechanisms formed in the elastomer. However, such interfitting or mating structures may present problems because the elastomer component may deform and disengage when the assembly is subjected to forces tending to separate the components.

Figure 5A:
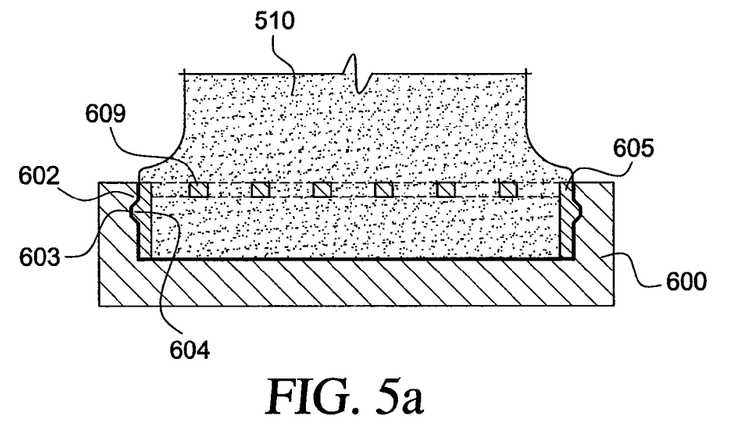
FIG. 5a is a partial detail sectional view of assembled intermediate perforated plate mechanical fixation means.
Figure 5B:
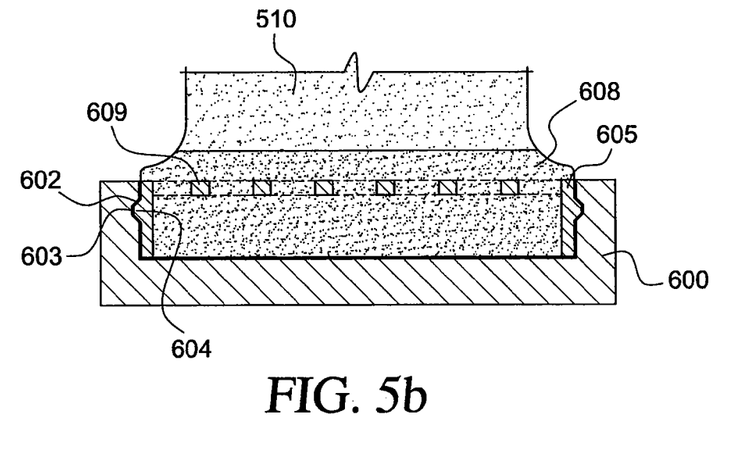
FIG. 5b is a partial detail sectional view of the embodiment of FIG. 5a illustrated in an alternate embodiment with a harder elastomer secured to the intermediate perforated plate mechanical fixation means.

In contrast to such conventional assemblies, the method and devices of the invention permit the construction of modular components that can be readily assembled, yet resist disengagement of the elastomer component. Such devices may use an intermediate (and preferably rigid) anchoring structure 605 as illustrated in the embodiments of FIGS. 5a and 5b. In the form shown, the anchoring structure 605 is constituted by a dependent peripheral flange of a perforated plate 609. A rigid plate 600 is provided with peripheral mechanical means of fixation 602, illustrated by groove 603 that engages a protrusion 604 of intermediate anchoring structure 605, thereby forming a secure connection between the two rigid structures, i.e., rigid (e.g., metal) anchoring structure 605 and rigid (e.g., metal) substrate 600. The intermediate anchoring structure 605 may be unitary with the porous attachment structure (e.g., plate 609), as shown, or the porous attachment structure and anchoring structure may be formed as discrete components that are attached to each other. Elastomer core 510 is securely fixed to intermediate anchoring structure 605 by porous structures such as those described above and exemplified here by metal plate 609. In these embodiments the elastomeric core 510 is secured to the intermediate anchoring structure 605, which is in turn fixed to rigid endplate 600. It will be appreciated that this embodiment is useful for reduction of manufacturing inventory where the product family may require large numbers of varied polymer and rigid plate configurations. Thus, an assembly with the same polymer and intermediate anchoring means may be independently assembled to rigid endplates of several different sizes and designs.

FIG. 5b illustrates an embodiment wherein elastomer core 510 is bonded to a harder elastomer 608, which is secured (via plate 609) to the intermediate anchoring structure 605, which is in turn assembled to rigid endplate 600. Rigid endplate 600 has mechanical means of fixation 602 illustrated by a recess or groove 603 cooperating with a projection 604 of anchoring structure 605, thereby forming a secure connection with plate 600.

Figure 5C:
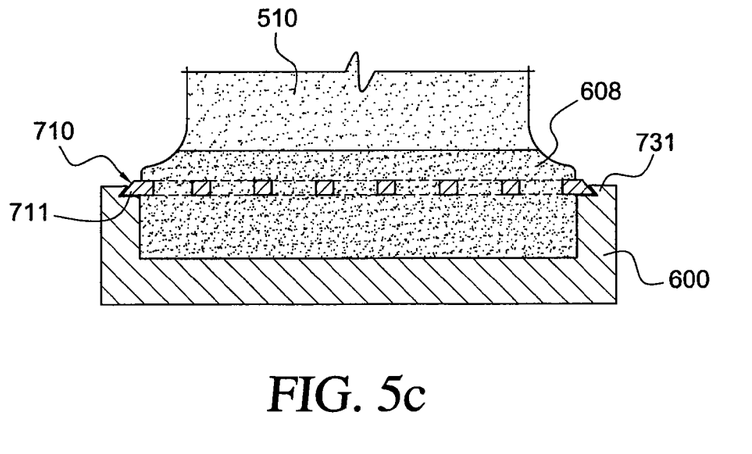
FIG. 5c is a partial detail sectional view showing a variation of the embodiment of FIG. 5b, having a slidable dovetail engagement of the intermediate perforated plate to the rigid endplate.

FIG. 5c illustrates an additional embodiment similar to that illustrated in FIG. 5b. In this embodiment the hard elastomer 608 is fixed to a typically metallic porous plate 710, which incorporates a male dovetail 711 securely engaging a female dovetail 731 formed on rigid endplate 600.

It will be appreciated that, in the each of the foregoing embodiments, the porous attachment structure is provided on the substrate member so as to cover a portion thereof, while the elastomeric material fills a major portion (>50%) of a volume adjacent to the covered portion of the substrate and containing the porous attachment structure. The elastomeric material is thereby firmly secured to the substrate. In embodiments having a porous attachment structure such as a plate, a screen, etc. that is spaced from a facing surface portion of the substrate, the entire volume between the porous attachment structure and the facing surface portion of the substrate may advantageously be filled with elastomer (as, for example, in FIGS. 4a, 4b, and 4d).

Figure 6A:
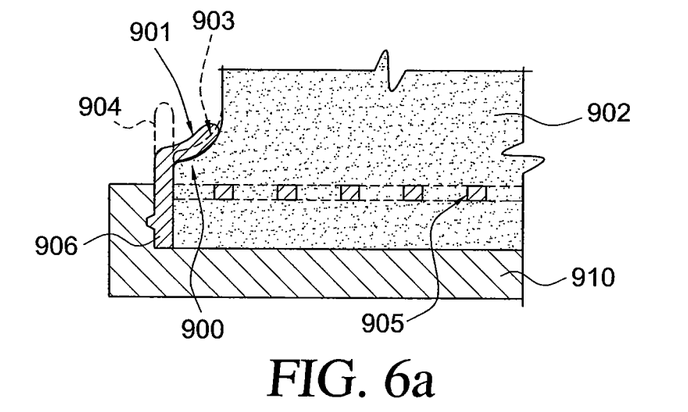
FIG. 6a is a detail partial cross section of an alternate embodiment of this invention having additional compressive fixation applied to a peripheral extension of the flexible core.
Figure 6B:
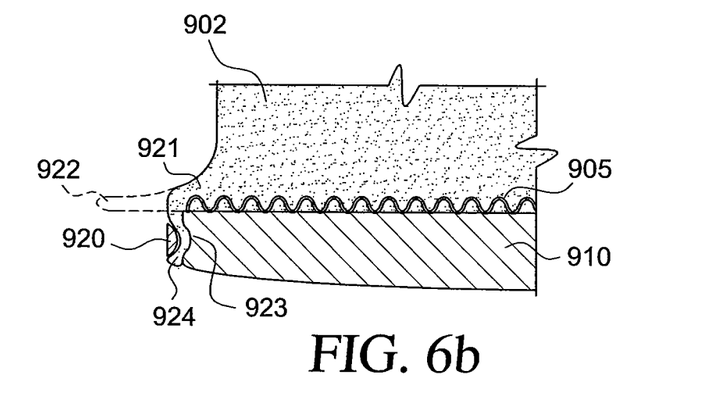
FIG. 6b is a detail partial cross section showing a variation of the embodiment of FIG. 6a, where compressive fixation is applied by a compression band.
Figure 6C:
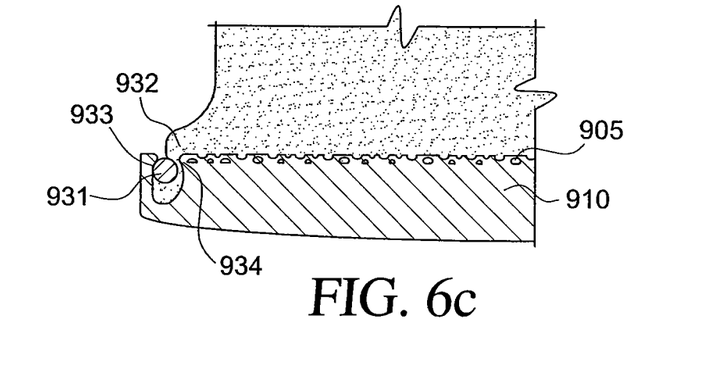
FIG. 6c is a detail partial cross section showing another variation, where compressive fixation is applied by a ring compressed against the peripheral extension of the flexible core.

FIGS. 6a-6c illustrate, in detail, a partial cross section of other embodiments of the invention having a rigid fixation structure 905, as discussed above, and additionally incorporating structure to compress a laterally extended elastomer flange against a rigid fixation structure for the elastomer or against a rigid substrate. In FIG. 6a a lateral extension of the elastomer core 902 is preferably fashioned as a flange 900 extending outwardly from the core 902. In this embodiment, the flange having original form indicated in phantom at 903 is compressed by a compressive element 901 having an original form indicated in phantom at 904. The deformed compressive element 901 is preferably integral to the rigid fixation means 906, as shown, but may be alternatively assembled to the prosthesis, after assembly of the elastomeric core and rigid endplate, in order to provide the desired compression. Flexible core 902 and flange element 903 are preformed, and subsequently compression element 904 is permanently deformed to the shape indicated at 901, thereby engaging and deforming flange element 903 to the compressed form 900. In this embodiment the compressive element 906 may be in the form of a peripheral band achieving compression by interference fit over the flexible core flange 901. Alternate embodiments may utilize screws, wires, clips, or other conventional fixation means in conjunction with a peripheral flange to provide the compressive force required to compress the flexible core flange.

FIG. 6b illustrates in detail, a partial cross section of an alternate embodiment of FIG. 6a, wherein a compression band 920 is assembled over flange 921 having an original form 922 and compresses flange 921 into groove 923 to a deformed shape 924.

FIG. 6c illustrates, in detail, a partial cross section of an alternate embodiment of FIG. 6a, wherein the compressive fixation is achieved by the forcible assembly of compression element 931, extending peripherally, between flange element 932 and an exterior peripheral retaining groove 933, whereby flange 932 is compressed against interior retaining groove 934 on rigid substrate 910.

Figure 7A:
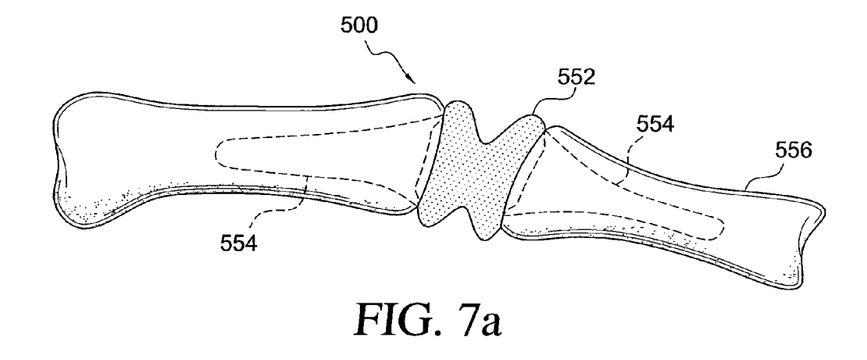
FIG. 7a illustrates an embodiment comprising an elastomeric joint prosthesis wherein the elastomeric member is attached to two hard, structural intramedullary members.
Figure 7B:
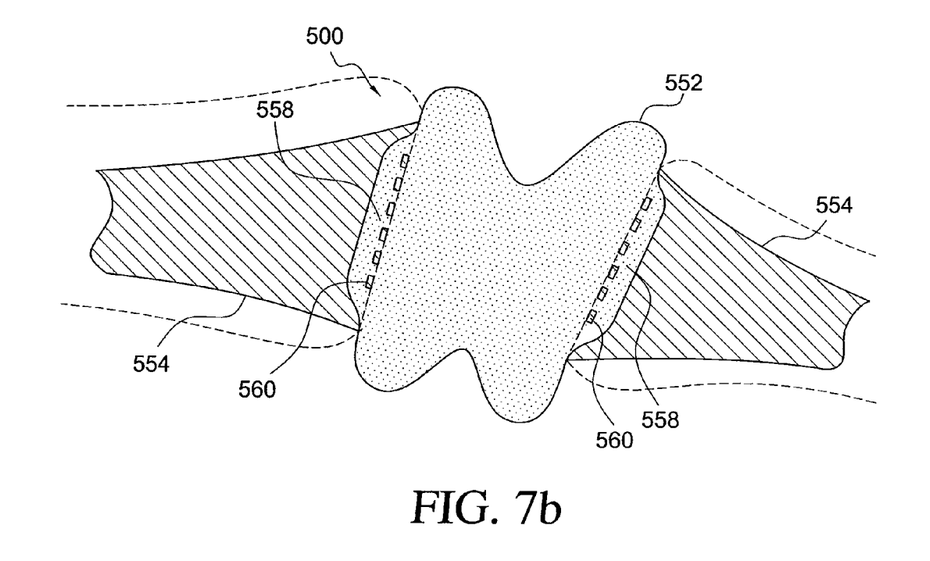
FIG. 7b is a sectional view of FIG. 13a showing the attachment of the elastomeric member to the two hard, structural intramedullary members.

FIGS. 7 and 7b illustrate an elastomeric joint prosthesis 550 according to the invention, suitable, e.g., as a prosthetic replacement for a finger joint. The prosthesis comprises a flexible elastomeric body 552 fastened to rigid intramedullary members 554, made of metal, rigid plastic, or the like, and inserted, by conventional procedures, into phalanges 556. The intramedullary members 554 are provided with recessed regions 558 at the appropriate ends thereof. Rigid perforated plates 560, made of metal, or the like (shown in phantom in FIG. 7a), extend across the ends of the intramedullary members 554, leaving a space between the perforated plate 560 and the body of the intramedullary member 554. The flexible elastomeric body 552 is molded or otherwise attached to the intramedullary members 554 so that the elastomeric material extends through each perforated plate 556 and forms a continuous layer of polymer material behind the plate 560 (best seen in the partial sectional detail, FIG. 7b).

Figure 8A:
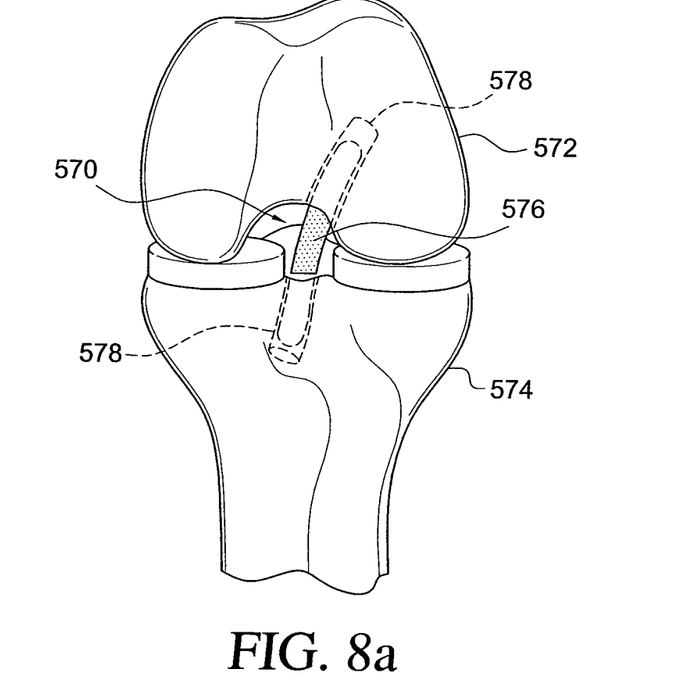
FIG. 8a illustrates an embodiment comprising an anterior cruciate replacement prosthesis in which the deformable elastomeric member is attached to two hard, bone fixation plugs.
Figure 8B:
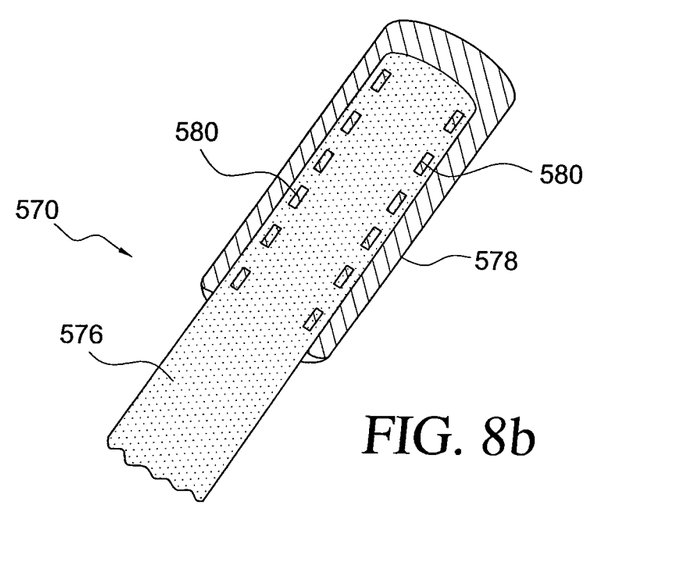
FIG. 8b is a sectional view through bony fixation members of FIG. 8a showing attachment of the deformable elastomeric member to the hard, bony fixation plugs.

FIGS. 8a and 8b illustrate a further prosthesis 570 according to the invention, suitable, e.g., as a prosthetic replacement for an anterior cruciate ligament of a knee joint or other ligament, a tendon or the like. FIG. 8a shows the ligament prosthesis 570, in partial phantom, implanted between the femur 572 and the tibia 574 of a knee joint. The prosthesis 570 comprises an elongated body 576, ends of which are provided with hard, rigid bone fixation plugs 578, which may be constructed of conventional materials and implanted by conventional techniques. As shown, and best seen in the partial sectional detail FIG. 8b, each of the bone fixation plugs 578 is preferably tubular, with perforated plates, or the like, 580 lying in respective planes substantially parallel to the plug axis and extending transversely across the lumen of the tubular plugs 578. The elastomeric body 576 is molded or otherwise attached to the bone fixation plug 578 so that the elastomeric material extends through each perforated plate 580 and forms a continuous layer of polymer material behind the plate 580.

Figure 9A:
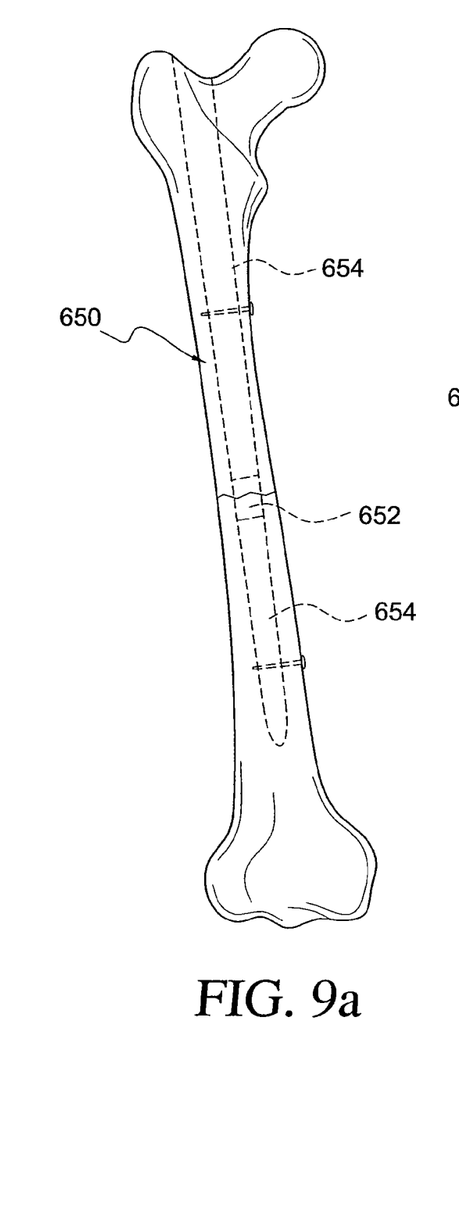
FIG. 9a illustrates an embodiment comprising an intramedullary fixation rod having a central low stiffness region in which a deformable elastomer is attached to the two ends of the rod.
Figure 9B:
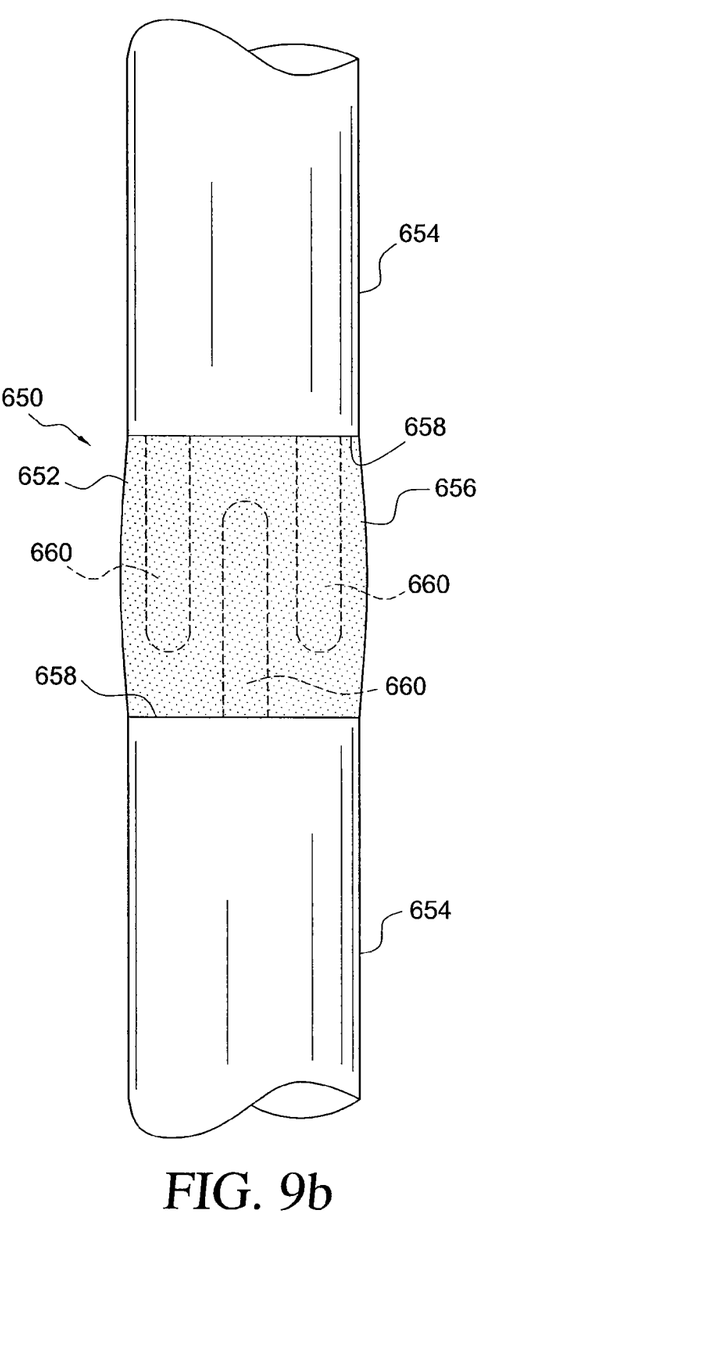
FIG. 9b is a sectional view through the central portion of the rod of FIG. 9a showing attachment of deformable elastomer to the hard rod ends.

FIGS. 9a and 9b illustrate an embodiment comprising an intramedullar fixation rod 650 for a long bone such as a femur, wherein the rod has a central low stiffness region 652 in which a deformable elastomer is interposed between two intramedullar portions 654 of the rod. FIG. 9b is a sectional view through the central region 652 of fixation rod 650 of FIG. 9a showing a segment of deformable elastomer 656 attached to the internal ends 658 of the intramedullar portions 654 of the fixation rod 650. The elastomer of the elastomer segment 656 is molded or otherwise attached to rigid perforated projections 660 (shown in phantom) extending from the internal ends 658 of the intramedullar portions 654, and extends through the perforations of the rigid projections 660 to form a unitary body holding together the intramedullary portions 654.

EXAMPLE

This example illustrates the additional strength and uniformity obtainable using an embodiment of the invention as compared with known fixation of elastomer to a rigid substrate having a layer of beads.

Test samples were prepared by attaching a cylindrical elastomeric core of 11.2 mm diameter and 4 mm length to two titanium alloy endplates such that the whole assembly could be tested in tension to failure. The elastomer used was 75 D durometer polycarbonate-polyurethane (Chronoflex-C, CardioTech Inc., Wilmington, Mass.), which was attached to the metal endplates, made of Ti-6% Al-4% V surgical alloy, through injection molding. The experiment examined different attachment means including a porous coating and a perforated plate configuration.

Two series of samples were tested, several samples of each series being tested:

A. Porous surface using a double layer of sintered beads of −45+60 diameter to provide a porosity of approximately 21%

B. Perforated surface with a regular array of 1.5 mm through-holes to provide a porosity of approximately 44%. The design provided for the elastomer to extend through the holes and to provide for a full sheet of 1 mm thick polymer on the far side Testing: All the samples were tested to failure in uni-axial tension at a rate of 2.5 mm/minute in a water bath maintained at a temperature of 37° C. to simulate physiological conditions. The results are presented in Table 1 below.

TABLE 1

| Sample | Attachment Means | Maximum Force (N) |
| --- | --- | --- |
| A | −45 + 60 Double Layer of Beads | 493 ± 42 |
| B | Perforated Plate | 811 ± 50 |

Conclusion from experiment: The use of a perforated plate to secure the elastomer to a metal structure provides for significantly greater fixation strength than can be achieved using a porous coated or beaded surface. As compared with porous coated or beaded surfaces, where pores are defined by spherical surfaces of beads or the like, advantages in attachment strength can be obtained by the use of structures in which pores are defined partially or wholly by non-spherical surfaces.

The invention having been described above in terms of certain embodiments, it will be apparent to those skilled in the art that many changes and alterations can be made without departing from the spirit or essential characteristics of the invention. The present disclosure is therefore to be considered as illustrative, and not restrictive, of the invention. Moreover, it will be appreciated from the above description that the invention provides a number of advantageous effects. For example, the invention generally provides for secure attachment of an elastomer to a rigid substrate. In a surgical implant, the invention provides increased fixation strength of a flexible elastomeric member to a rigid implant substrate member, such as an elastomeric core fixed to an endplate of a spinal disc prosthesis, without relying solely upon either a porous coating or an adhesive layer for attachment. The invention additionally provides a means of fixing elastomeric members to rigid members in a manner that allows for simpler manufacturing and for easier inspection of final product. Other advantages of the invention will be apparent to those skilled in the art.

We claim:

1. An intervertebral disc prosthesis implant, comprising:
a rigid surgical implant substrate comprising an intervertebral disc prosthesis endplate,
a porous attachment structure provided on said substrate and covering a portion of said substrate, said porous attachment structure including a perforated plate having a first major surface facing said portion of said substrate, a second major surface facing away from said portion of said substrate, and a periphery fastened to said substrate, and
an elastomeric disc prosthesis core body having a portion adjacent to said portion of said substrate and impregnating said porous attachment structure, said portion of said elastomeric intervertebral disc prosthesis core body filling a major portion of a volume bounded by said second major surface of said perforated plate and said portion of said substrate, whereby said elastomeric intervertebral disc prosthesis core body is secured to said substrate.

2. The implant of claim 1, wherein said porous attachment structure has a surface facing said portion of said substrate and spaced therefrom, and said elastomeric intervertebral disc prosthesis core body includes a continuous layer of elastomer covering a portion of said surface of said porous structure.

3. The implant of claim 2, wherein said continuous layer of elastomer is substantially coextensive with said portion of said substrate.

4. An intervertebral disc prosthesis implant, comprising:
a rigid surgical implant substrate comprising an intervertebral disc prosthesis endplate,
a porous attachment structure provided on said substrate and covering a portion of said substrate, and
an elastomeric intervertebral disc prosthesis core body having a portion adjacent to said portion of said substrate and impregnating said porous attachment structure,
wherein throughout a thickness of said porous attachment structure in planes generally parallel to said portion of said substrate, a net porosity of said porous structure is greater than 21.5%, and
wherein said porous attachment structure includes a perforated plate having a periphery fastened to said substrate.

5. The implant of claim 4, wherein said porous attachment structure has a surface facing said portion of said substrate and spaced therefrom, and said elastomeric intervertebral disc prosthesis core body includes a continuous layer of elastomer covering a portion of said surface of said porous structure.

6. The implant of claim 5, wherein said continuous layer of elastomer is substantially coextensive with said portion of said substrate.

7. The implant of claim 4, wherein said net porosity of said porous structure is in a range of about 30% to about 90%.

8. The implant of claim 7, wherein said net porosity of said porous structure is in a range of about 30% to about 80%.

9. The implant of claim 7, wherein said net porosity of said porous structure is in a range of about 30% to about 71%.

10. The implant of claim 7, wherein said net porosity of said porous structure is about 44%.

11. A method of manufacturing an intervertebral disc prosthesis, comprising:
providing a rigid intervertebral disc prosthesis endplate,
providing a porous attachment structure,
attaching said porous attachment structure to said intervertebral disc prosthesis endplate, and
impregnating said porous attachment structure with an elastomer to secure said elastomer to said rigid intervertebral disc prosthesis endplate,
wherein said porous attachment structure includes a perforated plate having a periphery fastened to said rigid intervertebral disc prosthesis endplate.

12. The method of claim 11, wherein said porous attachment structure is attached to said intervertebral disc prosthesis endplate so as to have a surface facing a portion of said intervertebral disc prosthesis endplate and spaced therefrom, and said elastomer includes a continuous layer of elastomer covering a portion of said surface of said porous structure.

13. The method of claim 12, wherein said continuous layer of elastomer is substantially coextensive with said portion of said intervertebral disc prosthesis endplate.

14. The method of claim 11, wherein said porous attachment structure is attached to said intervertebral disc prosthesis endplate so as to cover a portion of said intervertebral disc prosthesis endplate, and the impregnating is performed so as to form an elastomeric intervertebral disc prosthesis core body having a portion adjacent to said portion of said intervertebral disc prosthesis endplate, with said portion of said elastomeric body filling a major portion of a volume adjacent to said portion of said intervertebral disc prosthesis endplate and containing said porous attachment structure.

15. The method of claim 11, wherein said porous attachment structure is attached to said intervertebral disc prosthesis endplate so as to cover a portion of said intervertebral disc prosthesis endplate, and wherein throughout a thickness of said porous attachment structure in planes generally parallel to said portion of said intervertebral disc prosthesis endplate, a net porosity of said porous structure is greater than 21.5%.

16. An elastomeric intervertebral disc prosthesis, comprising
an elastomeric intervertebral disc core; and
superior and inferior rigid intervertebral disc endplates attached, respectively, to superior and inferior portions of said core;
said superior and inferior endplates each having:
an external surface configured for fixation to an adjacent vertebra; and
an internal surface provided, at least over a portion of said internal surface, with a porous attachment structure for attachment to the corresponding one of said superior and inferior portions of said core;
said porous attachment structure being integral with the corresponding endplate and being embedded within a volume of said elastomeric core adjacent to said internal surface;
wherein said porous attachment structure includes a perforated plate having a periphery fastened to said internal surface; and wherein, throughout a thickness of said porous attachment structure in planes generally parallel to said internal surface, a net porosity of said porous attachment structure is greater than 21.5%.

17. The intervertebral disc prosthesis of claim 16, wherein at least one of said endplates is provided with a generally peripheral rim upstanding from said internal surface, and
the periphery of the corresponding perforated plate is attached to said peripheral rim.

18. The intervertebral disc prosthesis of claim 17, wherein said perforated plate is spaced from said portion of said internal surface of the corresponding endplate, and
said elastomeric intervertebral disc core has a portion adjacent to said portion of said internal surface of said corresponding endplate and impregnating said perforated plate, said portion of said elastomeric intervertebral disc core filling a major portion of a volume adjacent to said portion of said internal surface of said corresponding endplate and containing said perforated plate, whereby said elastomeric intervertebral disc core is secured to said corresponding endplate.

19. A method of manufacturing an intervertebral disc prosthesis, comprising:

provoding a rigid intervertebral disc prosthesis endplate, and securing an intervertebral disc prosthesis elastomer core to said intervertebral disc prosthesis endplate via a porous attachment structure including a perforated plate, said perforated plate being impregnated with said elastomer and having a periphery fastened to said rigid intervertebral disc prosthesis endplate.

* * * * *